United States Patent [19]
Soest

[11] Patent Number: 5,703,960
[45] Date of Patent: Dec. 30, 1997

[54] LUMBER DEFECT SCANNING INCLUDING MULTI-DIMENSIONAL PATTERN RECOGNITION

[75] Inventor: Jon F. Soest, Seattle, Wash.

[73] Assignee: U.S. Natural Resources, Inc., Vancouver, Wash.

[21] Appl. No.: 714,632

[22] Filed: Sep. 16, 1996

Related U.S. Application Data

[63] Continuation of Ser. No. 296,348, Aug. 24, 1994, abandoned.

[51] Int. Cl.$^6$ .................................................... G06K 9/00
[52] U.S. Cl. ........................... 382/141; 382/108; 382/110; 348/91; 348/92; 250/559.18; 250/559.45
[58] Field of Search ................................ 382/100, 108, 382/110, 141, 143, 149, 181, 209, 224; 250/559.18, 559.45, 559.44; 356/430, 429, 431, 445, 446; 348/91, 92, 125, 128, 129, 130

[56] References Cited

U.S. PATENT DOCUMENTS

| | | | |
|---|---|---|---|
| 3,850,526 | 11/1974 | Corey, III | 356/109 |
| 3,922,093 | 11/1975 | Dandliker et al. | 356/120 |
| 3,976,384 | 8/1976 | Matthews et al. | 356/200 |
| 4,276,910 | 7/1981 | Eichenberger | 139/273 |
| 4,606,645 | 8/1986 | Matthews et al. | 356/446 |
| 4,710,642 | 12/1987 | McNeil | 250/571 |
| 4,754,148 | 6/1988 | Barkowski et al. | 250/571 |
| 4,945,253 | 7/1990 | Frohardt | 250/571 |
| 5,252,836 | 10/1993 | Matthews et al. | 250/571 |
| 5,311,131 | 5/1994 | Smith | 324/309 |

OTHER PUBLICATIONS

Adel et al. "Evaluation of colour spaces in computer vision application of wood defects detection" Oct. 1993, pp. 499–504.
IEEE Conference Proceedings, 1993 International Conference on Systems, Man and Cybernetics.
A paper entitled "A Simple Optical Scanner For Grain Defects" dated Oct. 26, 1993.
An article from Analytical Chemistry, vol. 59, No. 9, May 1, 1987.
Brochure–Conference on Scanning Technology, et al Oct. 25–27, 1993 titled "Multivariate Image Analysis, et al".

*Primary Examiner*—Leo Boudreau
*Assistant Examiner*—Bipin Shawala
*Attorney, Agent, or Firm*—Robert L. Harrington

[57] ABSTRACT

Grain defect scanning takes into account a broad set of data representing both wood grain structure and wood grain image to provide a multi-dimensional scan vector for an inspection point with wide variation therein relative to defect types. A library of similarly structured multi-dimensional training set vectors developed during a preliminary training session with known defect types is referenced by multivariate pattern recognition analysis to classify a collection of scan vectors associated with an article under inspection. By statistically matching scan vectors with training set vectors under pattern recognition analysis, physical locations on a wood article are identified according to known defect types.

19 Claims, 4 Drawing Sheets

SCAN VECTOR

| | |
|---|---|
| X | X SPATIAL DIMENSION RELATIVE TO ARTICLE |
| Y | Y SPATIAL DIMENSION RELATIVE TO ARTICLE |
| S | MAGNITUDE OF SPECTRAL DETECTOR OUTPUT S |
| T | MAGNITUDE OF TRACHEID EFFECT DETECTOR OUTPUT T |
| H | HEIGHT OF INSPECTION POINT |
| S/R | CALCULATED RATIO OF OUTPUTS S AND R |
| C1 | MEASURED LIGHT INTENSITY IN FIRST COLOR |
| C2 | MEASURED LIGHT INTENSITY IN SECOND COLOR |
| C3 | MEASURED LIGHT INTENSITY IN THIRD COLOR |
| R | MAGNITUDE OF RETRO DETECTOR OUTPUT R |

FIG. 6

TRAINING SET VECTOR

| | |
|---|---|
| N | NAME OF WOOD GRAIN CONDITION CHARACTERIZATION |
| S | MAGNITUDE OF SPECTRAL DETECTOR OUTPUT S |
| R | MAGNITUDE OF RETRO DETECTOR OUTPUT R |
| T | MAGNITUDE OF TRACHEID EFFECT DETECTOR OUTPUT T |
| H | HEIGHT OF INSPECTION POINT |
| S/R | CALCULATED RATIO OF OUTPUTS S AND R |
| C1 | LIGHT INTENSITY IN FIRST COLOR |
| C2 | LIGHT INTENSITY IN SECOND COLOR |
| C3 | LIGHT INTENSITY IN THIRD COLOR |
| F1 | FUNCTION MINIMIZING DATA POINTS |
| F2 | FUNCTION MINIMIZING DATA POINTS |
| F3 | FUNCTION MINIMIZING DATA POINTS |

5,703,960

LUMBER DEFECT SCANNING INCLUDING MULTI-DIMENSIONAL PATTERN RECOGNITION

This application is a continuation of application(s) Ser. No. 08/296,348 filed on Aug. 24, 1994 now abandoned.

BACKGROUND OF THE INVENTION

The present invention relates generally to wood product processing, and particularly to an automated method and apparatus for detection of defects and other abnormal conditions on the surface of lumber or other solid wood products.

Automatic detection of defects and abnormal conditions improves wood processing operations. Overall production efficiency and product quality increases by automatic defect detection and corresponding product grading, processing or remedial action. Unfortunately, many existing defect scanning techniques have been complex and not always suitable across a sufficiently broad set of defect types.

Attempts to apply image processing technology have generally failed to adequately identify defects in a wood article. In particular, image processing algorithms generally suffer from an inability to find or measure the size of defects and also suffer from misclassification, i.e., sometimes identifying a normal grain area inappropriately as a defective area. Typically, image processing algorithms suffer from a lack of data representative of wood cell structure. Image processing algorithms receive a massive volume of image-based data, i.e., data representing the intensity of color in various color bands at specific locations on a wood grain article. Unfortunately, such massive image-based data does not directly relate to the wood grain structures of interest. Accordingly, while image processing algorithms receive and process massive amounts of data, the algorithms suffer from lack of real information concerning the wood grain structures to be characterized. Thus, where image processing algorithms can, at best, emulate vision and analyze the resulting image, such emulation and analysis typically fails to accurately classify grain structures, i.e., differentiate between normal grain and abnormal or defective grain.

It would be desirable, therefore, to improve automated defect detection and reporting apparatus and methods to more accurately characterize wood grain conditions throughout a broad set of potential defects and wood grain structure conditions.

SUMMARY OF THE INVENTION

In accordance with the present invention, a method for identifying a defect relative to a given wood article begins by collecting a first set of data values characterizing a portion of a sample wood article surface, the portion of the sample wood article surface corresponding to a known defect. The data values collected include at least one value responsive to wood grain structure at the portion of said wood article. At least one mathematic function is then selected for application to the first set of data values, the mathematic function resulting in a given clustering of or distance between said data values according to multivariate pattern recognition analysis. The first set of data values and selected mathematic function thereby establish a training set. The next step employed under the present invention calls for collection of a second set of data values characterizing a portion of said given wood article. The second set of data values corresponds to the first set of data values and is also applicable the selected at least one mathematic function to indicate a clustering of or distance between the second set of data values. If the selected mathematic function indicates sufficiently minimum distance between the second set of data values at or below the given distance, then the portion of the given wood article is identified as corresponding to the known defect associated with the first set of data values.

In accordance with one aspect of the present invention, a method for detecting the presence of at least one of a set of wood cell structure conditions at a wood article surface includes a preliminary step of executing a training session wherein for each of said set of wood cell structure conditions at least one training vector is defined. Each training vector includes a designation of the associated wood cell structure condition and a set of training vector data values characterizing the associated wood cell structure condition. The method next includes executing a scanning procedure against inspection points of said given wood article wherein a scan vector is collected for each inspection point. Each scan vector includes location data indicating a physical location for the associated inspection point and includes a set of scan vector data values corresponding to said training vector data values. Under multivariate pattern recognition analysis, each scan vector is applied to a mathematical function associated with each training vector, i.e., a function sufficiently clustering or minimizing distance between data points of the training set vector. If the function causes similar clustering for a scan vector, then the location data associated with the scan vector may be further associated with the wood grain condition of the statistically corresponding training vector.

The present invention further provides a method identifying the condition of inspection points of a wood article surface by first scanning a plurality of inspection points of the wood article surface. The scanning step includes collection for each inspection point both reflective grain defect data and tracheid effect data. The process continues by identifying a first class of surface conditions by reference to the grain defect scanning data, and identifying a second class of surface conditions by reference to the tracheid effect data while excluding from consideration those inspection points identified as being said first class surface conditions.

The subject matter of the present invention is particularly pointed out and distinctly claimed in the concluding portion of this specification. However, both the organization and method of operation of the invention, together with further advantages and objects thereof, may best be understood by reference to the following description taken with the accompanying drawings wherein like reference characters refer to like elements.

BRIEF DESCRIPTION OF THE DRAWINGS

For a better understanding of the invention, and to show how the same may be carried into effect, reference will now be made, by way of example, to the accompanying drawings in which.

DETAILED DESCRIPTION OF THE PREFERRED EMBODIMENT

The present invention operates generally by point-to-point inspection of a wood article while collecting and storing a variety of information characterizing the wood article at each inspection point. Thus, for each inspection point on a given article a set or vector of multi-dimensional data is collected and stored. As may be appreciated, two spatial dimensions locate the inspection point on the wood article, i.e., X and Y locations relative to the wood article. Additional dimensions of data stored in association with each inspection point include information representing the structure of wood grain at the inspection point. Other measurement information, e.g., color and height, relative to the inspection point further augment multi-dimensional characterization of the inspection point.

By modeling the inspection point as a vector of such multi-dimensional information, multivariate pattern recognition techniques are applied to characterize the inspection point. In particular, information obtained at a given inspection point, i.e., a scan vector, is analyzed under multivariate analysis relative to data vectors of similar structure from a training set, i.e., a training set vector, to statistically correlate each scan vector with a defect or with clear wood. Because information provided in the scan vector relates directly to the structure of wood grain at the inspection point, methods of pattern recognition become more useful, i.e., more useful relative to use of such pattern recognition techniques using only imaged-based information, e.g., using only color of an inspection point. When used in conjunction with distinct defect scanning and detection techniques, each contributing to one or more dimensions of data, the scanning method of the present invention reliably and automatically scans a wood article to accurately detect and locate defect conditions therein.

The key to using multivariate pattern analysis is use of multi-dimensional data, i.e., a number of channels of data measured at essentially the same inspection point and at essentially the same time. Wide variation in response among the various channels for various defect conditions improves defect differentiation under pattern recognition techniques. The variation is not necessarily of one data channel relative to another data channel, but a scan vector viewed as a whole under multivariate analysis varies widely for one condition, e.g. a knot, relative to another condition, e.g., clear wood. Collecting relative to a given inspection point a variety of data channels, including both wood cell structure responsive signals and image responsive signals, improves wood grain condition distinction under pattern recognition analysis.

Multi-dimensional data values taken from a scan vector are applied to a function previously found to sufficiently cluster reference data, i.e., sufficiently minimize distance between data points in n-dimensional space for a training set vector obtained as reference data by measurement of a known grain structure condition. For example, a pre-defined training set vector for a "diving grain knot" associates a descriptor representing a "diving grain knot" with a collection of multi-dimensional data found to coincide with such defect. A function is then selected which clusters the data points of the training set vector. When the multi-dimensional data of the scan vector is applied to this function and similar clustering results, the inspection point associated with the scan vector is characterized according to the descriptor, e.g., diving grain knot, of the training set vector.

The following description will show a simplified method of obtaining a variety of information relative to an inspection point to define a vector of multi-dimensional data characterizing that portion of a wood article. In accordance with the present invention, such multi-dimensional data includes data representative of wood grain structures at the inspection point, height of the inspection point, and image-based information, e.g., representing color intensity of the inspection point in various color bands. Overall, a robust and widely varying collection of data characterizes both the image and wood grain structure at each inspection point thereby supporting successful application of such multi-dimensional data to pattern recognition analysis.

Figure 1:
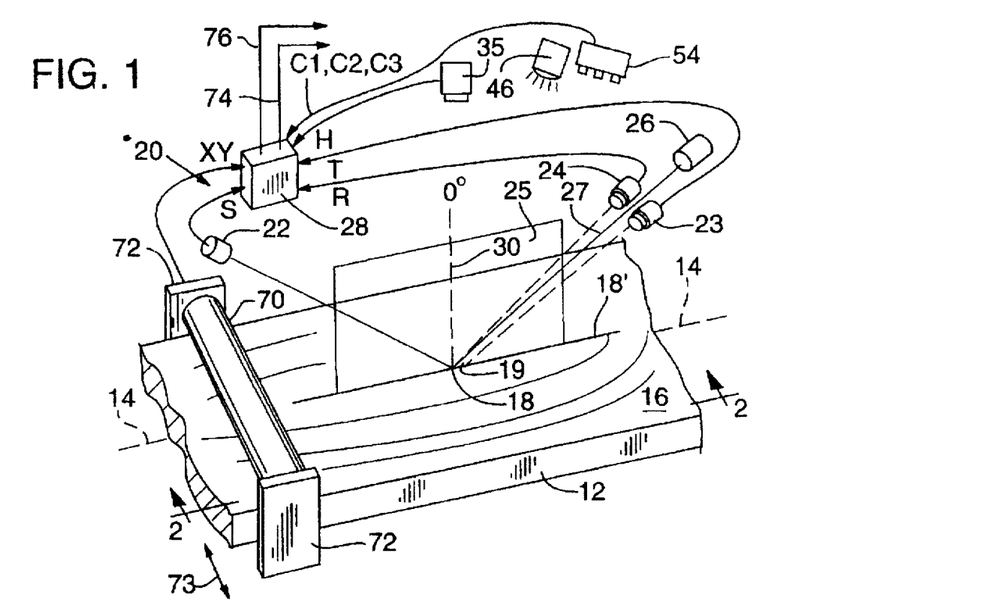
FIG. 1 illustrates a scanning apparatus collecting multi-dimensional information relative to a wood article and including information representative of article grain structure and of article image.
Figure 2:
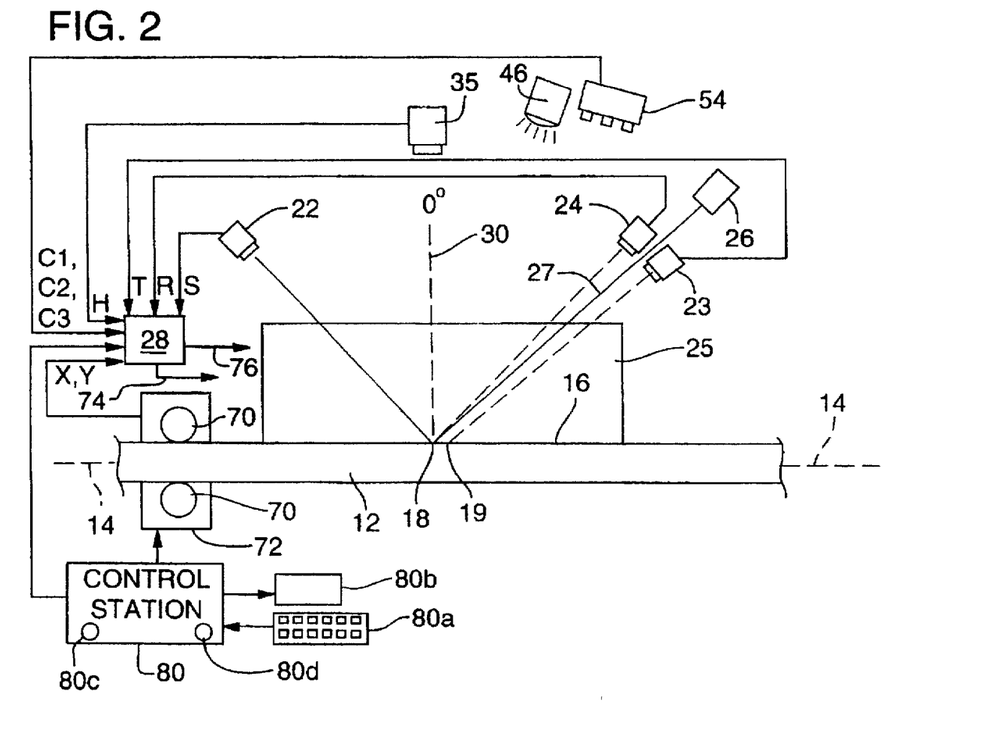
FIG. 2 illustrates a side view of the apparatus of FIG. 1 as taken along lines 2—2 of FIG. 1.

FIGS. 1 and 2 illustrate an apparatus 20 collecting inspection point information. A first source of grain structure related information used under the present invention is obtained by reflective grain defect scanning. The apparatus 20 and reflective grain defect scanning technique illustrated in FIGS. 1 and 2 is more fully described and illustrated in U.S. Pat. No. 5,252,836 filed by applicants Matthews et al under application Ser. No. 07/906,537 on Jun. 30, 1992 and issued in the name of the assignee of the present invention on Oct. 12, 1993. The disclosure of U.S. Pat. No. 5,252,836 is incorporated herein fully by reference thereto.

Generally, the method of grain detection and characterization shown in U.S. Pat. No. 5,252,836 shall be referred to herein as "reflective grain defect scanning" and described generally as follows. For a complete discussion of reflective grain defect scanning including most desirable angles of orientation for detectors 22 and 24 a more practical flying-spot implementation, and methods of employing data obtained therefrom, U.S. Pat. No. 5,252,836 should be consulted. Accordingly, only a general description of reflective grain defect scanning need be presented herein in support of the present invention.

Reflective grain defect scanning is particularly well adapted for detection and precise size measurement of grain defects, e.g., knots. Data obtained from reflective grain defect scanning provides not only the precise location of grain defects, but also precise measurement of the size of such grain defects. As discussed more fully hereafter, reflective grain defect scanning may be employed to first identify those defects, e.g., knots, for which it is best suited. Once this class of grain defects are identified, located, and measured precisely in size, the remaining portions of wood article 12 may be subjected to other methods of analysis, e.g., methods best suited for detection of remaining types of defects, e.g., defects other than knots. Reflective grain defect scanning is also very sensitive to early wood/late wood grain patterns and is therefore well suited for differentiating flat and vertical wood grain patterns.

FIGS. 1 and 2 illustrate defect detection apparatus 20 using, among other methods, reflective grain defect scanning. In FIGS. 1 and 2, an elongate wood grain article 12, having a longitudinal axis 14 and inspection surface 16, is subject to defect scanning at an inspection point 18 of surface 16. As used herein, the term "inspection point" shall refer to a point of incidence of scanning light directed upon an inspection surface, not necessarily a static point on the inspection surface 16. Article 12 has wood fiber cells lying substantially along its longitudinal axis 14, but may have grain defects or gross deviation from such normal direction of the wood fiber cells, e.g., knot wood. Apparatus 20 identifies by reflective grain defect scanning grain defects at the inspection point 18 of article 12.

Translation of article 12 relative to apparatus 20 and along longitudinal axis 14, e.g., as in longitudinal material feeding applications, provides grain defect scanning along a line 18' corresponding to a plurality of inspection points 18 as defined by such longitudinal movement of article 12 relative to apparatus 20. While an actual implementation of relative grain defect scanning might employ a more complex scanner arrangement, e.g., flying-spot laser scanning, the illustrations of FIG. 1 and 2 provide a fundamental understanding of reflective grain defect scanning and the nature of data obtained therefrom.

Apparatus 20 includes a pair of light detection devices, detector 22 and detector 24, each bearing upon inspection point 18 and lying along the line of material feed, i.e., in the plane of incidence 25 orthogonal to the surface 16 and containing the line 18'. As used herein, detector 22 shall be referred to as a specular detector providing an output S. Detector 24 is a retro-detector providing an output R. Detectors 22 and 24 lie generally symmetrically within a plane of incidence 25. The lines of sight to inspection point 18 for detection devices 22 and 24 are substantially symmetric about a vertical reference axis 30 within plane of incidence 25, normal to surface 16, and coincident with point 18. A light source 26 directs a collimated light beam 27, e.g., a low power laser beam, toward point 18 and substantially, as close as possible, along the line of sight between detector 24 and inspection point 18. Each detector 22 and 24 produces outputs S and R representing a level of reflected light energy detected. A discrimination circuit 28 receives the outputs S and R from detectors 22 and 24, respectively, for each inspection point 18 scanned.

As explained more fully in U.S. Pat. No. 5,252,836, light beam 27 reflects from surface 16 according to two models of reflection, i.e., specular and/or diffuse reflection. Generally, if inspection point 18 corresponds to a well behaved grain pattern, then the specular model of light reflection dominates. If, however, inspection point 18 corresponds to defective grain structure, then the diffuse reflection model dominates. If detectors 22 and 24 indicate reflected light of substantially the same magnitude intensity, i.e., the ratio S/R approximately equal to unity, then the diffuse light reflection model applies and the inspection point 18 is taken to correspond to a wood grain defect. If, however, the specular detector 22 receives more light than that of retro-detector 24, i.e., the ratio S/R is greater than unity, then the specular light reflection model dominates, indicating a normal wood grain pattern. Comparing the ratio S/R to a threshold value characterizes wood grain structures as normal or abnormal at the inspection point 18.

Thus, the methods and apparatus of reflective grain defect scanning provide information representing the structure of wood grain at a given inspection point 18. Given an understanding of the disclosure of U.S. Pat. No. 5,252,836, it will be understood that reflective grain defect scanning provides a stream of data characterizing a wood article. In particular, for each wood article scanned, a collection of samples are obtained. Each sample includes a sequence of information beginning with an X value and a Y value representing the position of the associated inspection point 18 relative to the surface 16 of the wood article 12. Additional information stored in each sample includes an output S magnitude, an output R magnitude, and a calculated S/R ratio. As used in the disclosure of U.S. Pat. No. 5,252,836, the ratio S/R is compared to a given threshold value to detect a ratio substantially equal to unity, i.e., to discriminate between normal and defective grain patterns. Under the present invention, however, it is suggested that the magnitude of outputs S and R be preserved for use in later pattern recognition algorithms. Preserving the magnitude of detector outputs S and R as multi-dimensional data applied to pattern recognition algorithms increases data channel variation as a function of defect type as is desirable in pattern recognition algorithms.

While use of reflective grain defect scanning has proven successful in grain defect detection, the present invention incorporates additional information into each inspection point sample, i.e., additional data dimensions, as a function of other information channels characterizing the inspection point 18.

One category of grain structure information collected relative to inspection point 18 is based on the "tracheid effect." U.S. Pat. No. 3,976,384 filed Jan. 16, 1975, issued Aug. 24, 1976 and entitled METHOD AND APPARATUS FOR DETECTING TIMBER DEFECTS describes the tracheid effect and its use in detecting wood grain defects. The disclosure of U.S. Pat. No. , 3,976,384 is incorporated herein fully by reference thereto.

Generally, the tracheid effect results from transmission of light within a wood article more freely along and within the cell structure rather than transverse to the cell structure. The tracheid effect is more obvious in softwoods, in the direction of the long, hollow tracheid cells that comprise most of the softwood structure. Light impinging a wood surface scatters into the cell structures, but scatters more freely along the length of cells then transverse to the cells. Light traveling transverse to the longitudinal axis of the cells quickly encounters cell walls and light transmission in this direction is restricted. As a result, light scattering within a wood article having normal grain structure produces a characteristic oval pattern lying along the longitudinal axis of the cell structures. Wood grain of abnormal structure, however, tends to be uniformly diffuse from the point of light entry into the wood article, and a characteristic circular region surrounding the point of light entry results.

Measurement of the tracheid effect is accomplished by a variety of mechanisms, U.S. Pat. No. 3,976,384 showing one such mechanism. Generally, by measuring the light intensity at a location very near the point of light entry and along the normal cell length indicates whether the characteristic oval pattern exists or the characteristic circular pattern exists. More particularly, given an average cell length of two to three millimeters, the characteristic oval pattern should produce at a distance of approximately two to three millimeters from the point of light entry and along the normal grain pattern a relatively greater light intensity. Similarly, if the grain structure is abnormal, then light intensity at a location approximately two to three millimeters from the point of light entry and along the normal grain pattern is relatively low. Thus, an apparatus measuring the tracheid effect detects a magnitude of light intensity at a location adjacent to, e.g., two to three millimeters, and along the normal grain pattern from the point of light entry into the wood article. By incorporating the measurement of the tracheid effect into a collection of other data representing cell structure at a given inspection point, a more comprehensive and robust characterization of the cell structure results.

In FIGS. 1 and 2, light detector 23 in a first form represents a high precision imaging optics light detector, directed generally toward the inspection point 18, focusing with high precision at an adjacent inspection point 19. More particularly, inspection point 19 lies along the longitudinal axis 14 of wood article 12 relative to inspection point 18 at a distance corresponding to the length of cell structures within the wood article 12, e.g., at a distance of approximately two to three millimeters for softwoods.

As may be appreciated, such first form of light detector 23 must have precise imaging optics capable of focusing at the inspection point 19, near the much brighter inspection point 18, to accurately detect a magnitude of light intensity representative of light transmitted through wood article 12. If light intensity at inspection point 19 is of given magnitude, one assumes that such intensity results from light transmission along and through normal cell structures, i.e., cell structures at inspection point 18 oriented generally along the longitudinal axis 14 of wood article 12. Light intensity below this given magnitude, however, indicates blockage of light transmission within wood article 12 and along axis 14 implying an abnormal cell structure, i.e., not well oriented along the longitudinal axis 14 of wood article 12.

Detector 23 in FIGS. 1 and 2 also represents an alternative less complex and less expensive form, i.e., not requiring a high precision imaging optics light detector. In particular, the tracheid effect is useful in detecting presence of a variety of wood surface conditions including small-area defects, e.g., knots, and broad-area defects, e.g., stains, wood decay, and compression wood. A high precision form of detector 23 is required for detection and measurement of small-area defects, but a lower resolution form of detector 23 will suffice for detection and measurement of broad-area defects. By use of a mask in detector 23 obscuring the inspection point 18 and by use of a relatively lower resolution and broader focusing light detection device, e.g., a large-aperture photodiode, one detects and measures broad-area defects by tracheid effect analysis.

As will explained more fully hereafter, by collecting in conjunction with the tracheid effect measurement other wood grain structure information, such as provided by the above-described grain defect scanning method and apparatus, the less complex and less expensive form of tracheid effect detector 23 may be employed. More particularly, the above-described grain defect scanning method and apparatus may be used to find and measure certain defects, e.g., knots, and provide a basis for excluding data for such portions of surface 16 from tracheid analysis. Excluding grain defects such as knots, leaves for analysis the broad-area defects which may be adequately detected using the lower resolution, less precise form of tracheid detector 23. Under such method, the detector 23 output T is collected for each inspection point 18, but when using the less precise form of tracheid effect detector 23 those inspection points 18 associated with certain defects, e.g. knots, as indicated by the reflective grain defect scanning method and apparatus, can be ignored when seeking broad-area defects based on output T.

Thus, the tracheid effect is analyzed on a point-by-point basis whereby for each inspection point 18, representing a point of light entry into wood article 12, an adjacent inspection point 19 is viewed and a magnitude of light intensity measured thereat. While the tracheid effect may be applied to a binary decision or choice between normal wood and abnormal wood, i.e., by comparing the measured intensity at inspection point 19 to a given threshold light intensity differentiating normal wood from abnormal wood, the magnitude of light intensity measured at a given inspection point 19 should be preserved. Applying a threshold comparison and preserving only the binary result represents a loss of information relative to cell structure characterization. Preserving magnitude information provides greater variation in detector response, and therefore greater utility in subsequent pattern recognition analysis. Accordingly, detector 23 output T represents a magnitude of light intensity measured at inspection point 19 for each inspection point 18 scanned by the apparatus 20.

The height of surface 16, in particular inspection point 18, can be measured by scanning apparatus 20 through the use of commonly available triangulation techniques. As may be appreciated, the height of inspection point 18, e.g., especially when coincident to a crack or split in article 12, affects other measurements taken by scanning apparatus 20. Collecting a height datum for each inspection point 18 augments the collection of multi-dimensional information associated with inspection point 18, and thereby further enhances pattern recognition algorithms applied thereto. Accordingly, a triangulation light detector 35 calculates a height of inspection point 18 and provides its output H to the discrimination circuit 28. Light detector 35 represents a variety of well known methods for detecting the height of inspection point 18. For example, a detector placed at a given angle relative to the light beam 27, e.g., 45 degrees, views inspection point 18 by focusing against a CCD array. The location of the resulting image on the CCD array relative to an expected location, e.g., corresponding to a reference height for inspection point 18, provides representation of the height of inspection point 18. It will be understood, however, that output H provided to discrimination circuit 28 may be provided by a variety of well known height detection methods.

As will be apparent to those skilled in the art, by suitably indexing the position of article 12 relative to apparatus 20 and collecting detector outputs S, R, T, and H in association with a given inspection point 18, a diverse set of widely varying information representing grain structure at the inspection point 18 is stored in a scan vector. Thus, for each indexed position of article 12 a scan vector of multi-dimensional data is associated with a corresponding inspection point 18. Indexing rollers 70 contact the upper surface 16 and lower surface of article 12 and roller control 72 moves article 12, by way of rollers 70, in indexed fashion while providing inspection point 18 location output X,Y to discrimination circuit 28. Discrimination circuit 28 then associates a physical location on surface 16 with the inspection point 18 for each indexed position of article 12. By such association, a scan vector holding a collection of grain structure representative data taken relative to inspection point 18 may be associated with a specific physical location, expressed in X and Y dimensions, relative to wood article 12. Multiple longitudinal scanning passes, but across different width portions of surface 16, as indicated by lateral indexing 73, provides scan vectors for the entire surface 16. Discrimination circuit 28 thereby constructs a data representation 74 of surface 16 as a collection of scan vectors.

Figure 3:
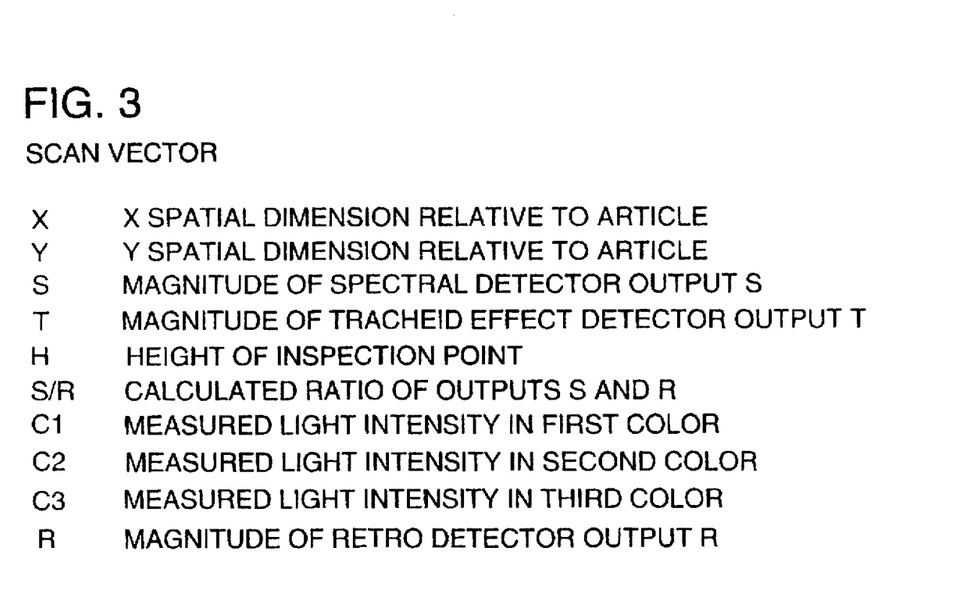
FIG. 3 illustrates a scan vector of multi-dimensional data collected by the apparatus of FIG. 1 relative to a specific inspection point of a wood article.

FIG. 3 illustrates the structure of a scan vector. Each scan vector represents a multi-dimensional characterization of the corresponding inspection point 18 including dimensions X, Y, S, R, T, and H. As may be appreciated, data representation 74 comprises a plurality of such scan vectors, each scan vector corresponding to one inspection point 18 of wood article 12. Discrimination circuit 28 also calculates additional fields for each scan vector as a function of such detector outputs. For example, a calculated S/R ratio may be incorporated into each scan vector.

In addition to data representing cell structure, traditional image-based information is collected for each inspection point 18. Accordingly, a white light source 46 illuminates surface 16 at the inspection point 18. A three-color light detector 54 views inspection point 18 and, with appropriate filtering, measures light intensity in each of a first, second, and third color band, e.g., measures green, red and blue light intensity. Corresponding detector 54 outputs C1, C2, and C3 are delivered to discriminator circuit 28 to augment characterization of the inspection point 18. Accordingly, each scan vector (FIG. 3) developed by discrimination circuit 28 in association with each inspection point 18 further includes fields C1, C2, and C3 characterizing the color intensity of inspection point 18 in each of a first, second, and third color band. Use of detector 54 to detect light intensity in each of three separate color bands is well known in the art and available in commercial products. Generally, appropriate filtering and processing of light intensity information, taking into account the presence of laser light illumination at inspection point 18, provides accurate representation of the color intensity of inspection point 18 in each of three separate color bands.

Figure 4:
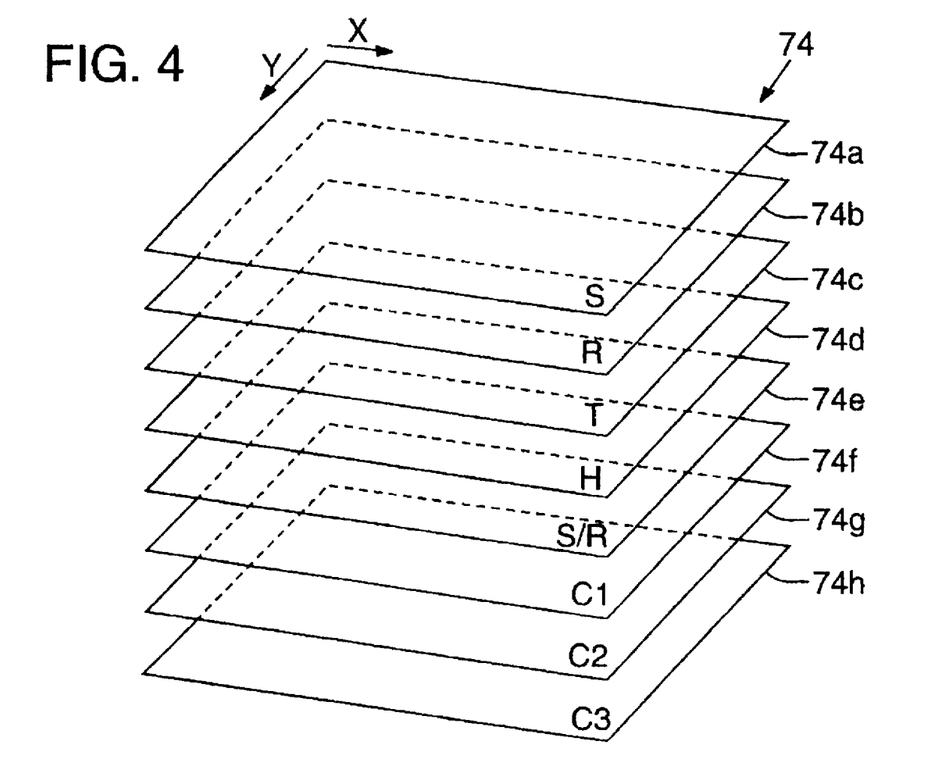
FIG. 4 illustrates a data representation of a wood article as provided by the apparatus of FIG. 1 and comprising a collection of scan vectors as shown in FIG. 3.

FIG. 4 illustrates graphically the data representation 74 of wood article 12. In FIG. 4, data representation 74 appears as a collection of two dimensional data structures, individually labeled 74a–74 h. Each of structures 74a–74h include cells addressed in X and Y dimensions corresponding to X and Y dimensions for location of inspection points 18 relative to wood article 12 surface 16. Each of structures 74a–74h correspond to one of the apparatus 20 values S, R, T, H, S/R, C1, C2, and C3, respectively. Thus, a single scan record vector resides throughout the data structures 4a–74h at corresponding X and Y locations therein. By collecting from data representation 74 a scan vector, i.e., a set of values at corresponding X and Y locations in each of structures 74a–74h, one obtains a scan vector corresponding to one inspection point 18. It will be appreciated by those skilled in the art that a variety of data representations may be employed to store and access a collection of scan vectors whereby each scan vector characterizes an inspection point 18 according to the values S, R, T, H, S/R, C1, C2, and C3.

Figure 5:
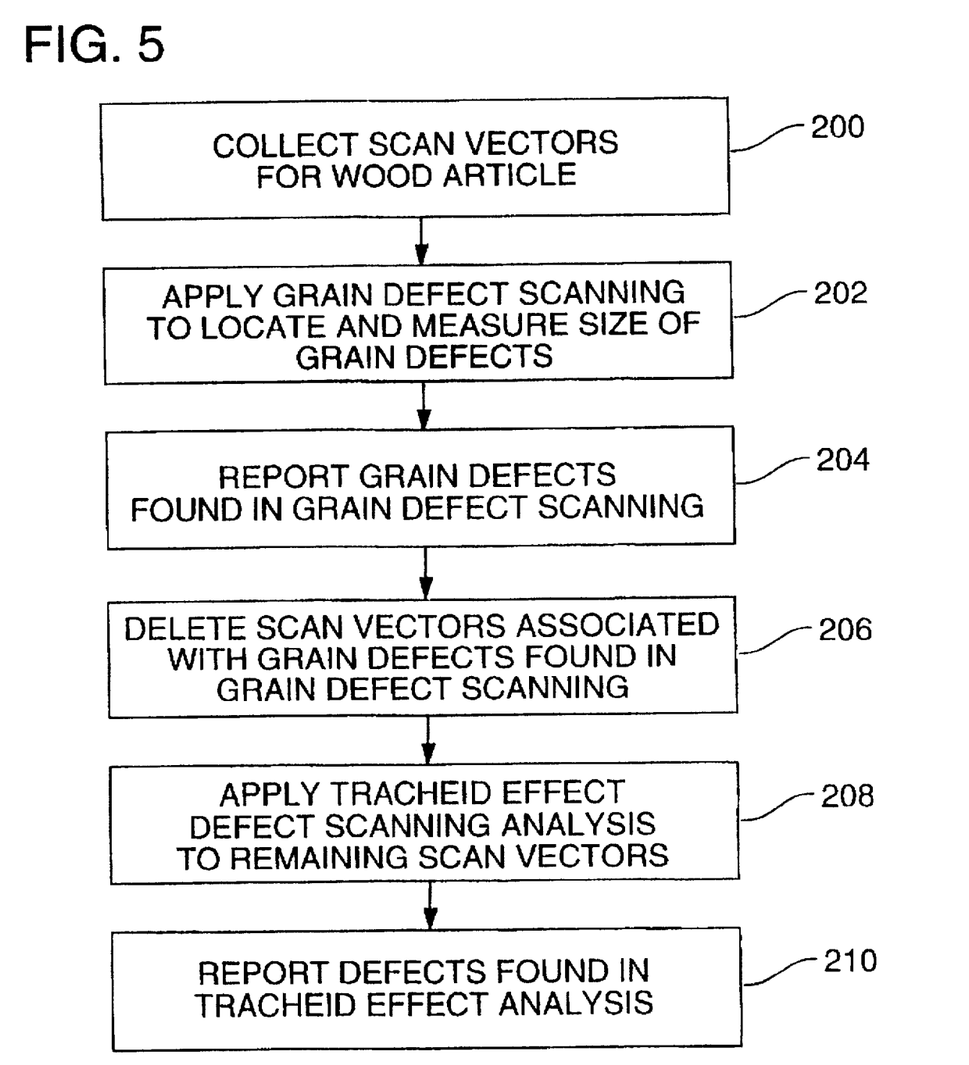
FIG. 5 illustrates a first use of the data representation portrayed in FIG. 4 wherein certain detector outputs identify defects best identified by such data and remaining detector outputs identify defects best identified by remaining detector data.

FIG. 5 illustrates by flow chart a first use of the data representation 74 for a given wood article 12. In FIG. 5, processing begins in block 200 where apparatus 20 collects scan vectors for a given wood article 12, i.e., builds a data representation 74. Continuing to block 202, the method of grain defect scanning is applied to the collection of scan vectors to locate and measure the size of grain defects. As noted above, reflective grain defect scanning is well suited for locating and measuring the size of grain defects such as knots. In block 204, the result of grain defect scanning analysis is reported, i.e., the location and size of knots as found under grain defect scanning is collected for later use. As may be appreciated, only a portion of the scan vector fields need be used to execute reflective grain defect scanning, i.e., fields S, R, and S/R of the scan vector provide sufficient basis to execute reflective grain defect scanning. Continuing to block 206, those scan vectors associated with defects found under reflective grain defect scanning are deleted from the collection of scan vectors, i.e., removed or masked from data representation 74. Because the corresponding portions of wood article 12 have been accurately located and measured in size, further consideration of this data is unnecessary. In block 208, the method of tracheid effect analysis is applied to the remaining scan vectors. As noted herein above, by first eliminating from consideration scan vectors associated with grain defects located and measured under reflective grain defect scanning, use of a relatively less complex, i.e., lower resolution, detector 23 is feasible. Eliminating scan vectors associated with defects found under reflective grain defect scanning relieves the subsequent process of tracheid effect analysis by limiting responsibility of such analysis to identification of only broad-area defects, e.g., stains, wood decay, and compression wood. Such broad-area defects are adequately identified through tracheid effect analysis using the above-described relatively lower resolution form of detector 23. Continuing to block 210, those defects found under tracheid effect analysis are reported.

Thus, the process illustrated in FIG. 5 uses certain data for identifying those defects best represented by that data, and uses other data for other defects best represented by such other data. As may be appreciated, the process illustrated in FIG. 5 may be further modified to incorporate additional data, e.g., color outputs C1, C2, and C3, for detection of conditions best represented by such data.

The data representation 74 is subjected to pattern recognition analysis whereby scan vectors taken from representation 74 are analyzed relative to redefined training set vectors established during a preliminary training session. More particularly, a relationship found to minimize distance among values in a training set is applied to the values of a scan vector; and if similar minimized distance among values in the scan vector results then the scan vector "statistically matches" the training set vector. In this manner, the multidimensional data of a scan vector, other than the positional X and Y location data, establishes through mathematic analysis characterization of a given inspection point 18.

Figure 6:
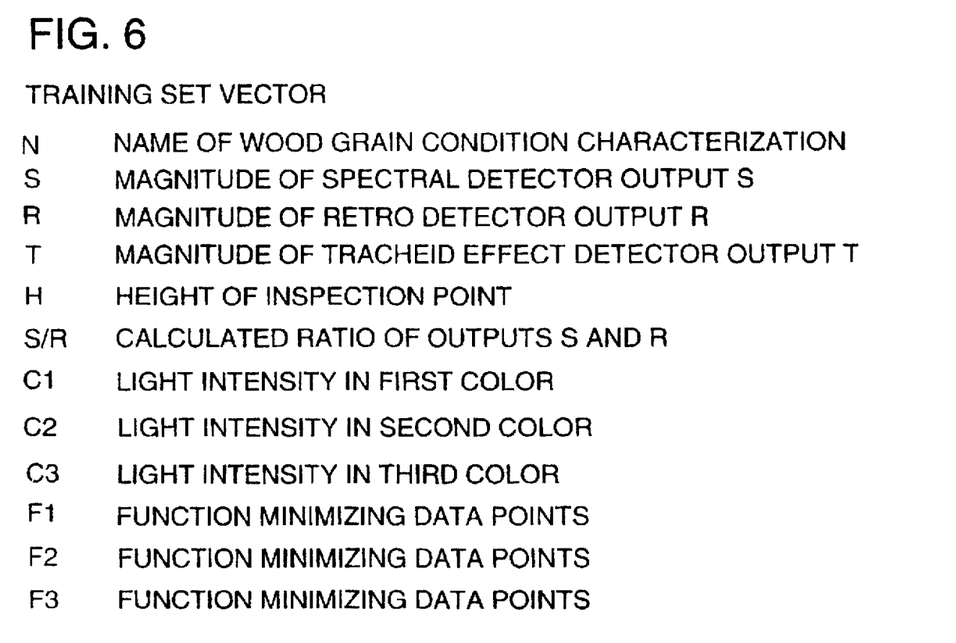
FIG. 6 illustrates a training set vector of generally similar structure to that of the scan vector of FIG. 3, but holding data and mathematic functions characterizing a known grain structure or defect as developed in a training session in anticipation of a pattern recognition analysis.

FIG. 6 illustrates the structure of a training set vector as contemplated under the present invention. The training set vector corresponds in structure to that of the scan vector, with the exception of the X and Y location data and the inclusion of additional fields representing selected mathematical functions. As may be appreciated, the X and Y location data becomes relevant when necessary to reference a particular location on wood article 12 in light of a characterization thereof following pattern recognition analysis. Each training set vector also includes a name field N representing the wood grain condition characterized by that training set vector. For example, a training set vector may represent a "live knot" and the name field N identifies that training set vector as one representing that particular wood grain structure. Once a training set vector is statistically matched with a scan vector, the X and Y location data taken from the scan vector is associated with the name field N taken from the statistically matching training set vector, thereby providing characterization of a particular physical location of article 12 surface 16.

To develop a collection of training set vectors for use in pattern recognition applied to the data representation 74, a "training" session is executed wherein an operator of apparatus 20 associates selected inspection points 18 with known wood grain structures, e.g., particular types of defects or normal grain patterns. Thus, a control station 80 (shown only in FIG. 2) drives roller control 72 and lateral indexing 73 enabling the operator thereof to feed sample articles 12, with examples of known defects or clear wood conditions, through scanning apparatus 20.

Once a data representation 74 for a sample wood article is generated by apparatus 20, the operator executing the training set session observes the representation 74 on terminal screen 80b to identify within data representation 74 scan vectors associated with known defects of clear wood conditions exhibited by the sample article 12. Once such scan vectors are identified in the data representation 74, the operator actuates a selection button 80d to define the selected scan vectors as training set vectors for the particular defect or clear wood condition and also enters by way of keyboard 80a a name designation for the selected defect or clear wood condition. The selected training set vectors are then reported by station 80 to discrimination circuit 28. This process continues until the operator has defined and reported to discrimination circuit 28 a training set vector for each defect or clear wood condition exemplified by sample wood article 12.

In this manner, discrimination circuit 28 builds the name field and data fields for training set vectors as represented in FIG. 5, i.e., including a name field N designating the particular defect or condition represented by the remaining data fields S, R, T, H, S/R, C1, C2, and C3. As may be appreciated, multiple training set vectors may be associated with a single name field, i.e., the name field need not be unique among a group of training set vectors. As explained more fully hereafter, additional function fields in each training set vector identify one or more mathematical functions found to minimize the distance between the values held in the data fields. Function fields F1, F2, and F3 represent such one or more mathematical functions associated with each training set vector. It will be understood, however, that one or any number of such functions may be found to sufficiently minimize the distance between data values held in the fields S, R, T, H, S/R, C1, C2, and C3. Upon termination of the training session, discrimination circuit 28 holds a collection of training set vectors as the data representation 76.

Figure 7:
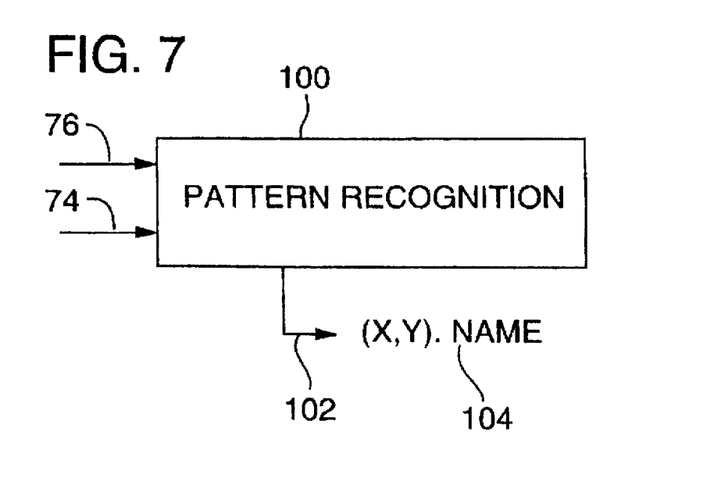
FIG. 7 illustrates application of the data representation of FIG. 4 and a collection of training set vectors as shown in FIG. 5 to a pattern recognition process providing as output characterization of grain structures at specific locations of a wood article.

In FIG. 7, once a training session is complete and a suitable collection of training set vectors organized as the data representation 76, a pattern recognition process 100 receives the data representation 74 for a particular wood article 12. By analyzing under multivariate analysis the data representation 74, a collection of scan vectors, against the data representation 76, a collection of training set vectors, each inspection point 18 is characterized. Generally, each portion of the wood article 12, e.g., as represented by a scan vector, is analyzed by reference to the collection of training set vectors. By employing pattern recognition analysis 100, the scan vectors of data representation 74 are statistically matched to the training set vectors of data representation 76. Upon finding a statistical match therebetween, the name field N of a statistically matching training set vector is associated with the X and Y dimensions of the matching scan vector whereby a particular location on a wood article 12 is associated with a wood condition characterization, i.e., associated with the name field N of a statistically similar training set vector. Thus, pattern recognition analysis 100 provides as output 102 a series of datum pairs 104 each pair comprising an X,Y location taken from a scan vector and an associated wood condition characterization as taken from a statistically matching training set vector. Given a sequence of such datum pairs 104 for a given wood article 12, the entire article 12 is represented by characterization of specific physical locations thereon according to, for example, known defect types. Subsequent processing steps, taking into account characterization of specific locations of wood article 12 advantageously make use of or grade wood article 12 accordingly.

The following discussion describes generally the process of multivariate analysis under pattern recognition analysis 100 of the present invention. It will be understood, however, that this class of mathematical analysis is well known and may be implemented in a variety of ways once the scan vectors and training set vectors are collected and prepared for use. U.S. Pat. No. 5,311,131 filed May 15, 1992 by applicant Justin P. Smith, entitled MAGNETIC RESONANCE IMAGING USING PATTERN RECOGNITION, and issued May 10, 1994 discusses generally the use of similar pattern recognition analysis, but applied to distinct data and in a distinct field of use. The disclosure of U.S. Pat. No. 5,311,131 may be referenced for the processing of training set vectors and scan vectors. In other words, the method of pattern recognition analysis proposed under the present invention may proceed in similar fashion to that shown in U.S. Pat. No. 5,311, 131. The method shown in U.S. Pat. No. 5,311,131 has as an objective, however, the presentation of an image whereas under the present invention system output comprises reporting of wood conditions at specific locations on a wood article. The disclosure of U.S. Pat. No. 5,311,131 is incorporated fully herein by reference thereto.

Generally, each training set vector is completed by identifying one of more functions which, when applied to the data therein, minimizes the distance therebetween. The process of identifying and developing such functions for representation in fields F1, F2, and F3 is well known to those familiar with multivariate pattern recognition analysis. To analyze a scan vector relative to a training set vector, therefore, the data fields of a scan vector are applied to a function taken from a training set vector, as represented by one of fields F1, F2, and F3, and if the result shows sufficiently minimum distance among data points then the scan vector statistically matches the training set vector.

Defect scanning such as described in U.S. Pat. 5,252,836, when combined with motion of a scanned article in a direction perpendicular to the scan, naturally gathers a two-dimensional array of data from one surface of the article. This array of data establishes multiple dimensions of data, for example the specular reflection, retroflection, thickness, color, or tracheid effect optical signals. At each inspection point, then, there is an n-dimensional vector of data representing the measured values of each of the signals from the inspection point.

One can more easily visualize data values and their significance in classification of each inspection point 18 when the data is one-dimensional or two-dimensional. For example, the technique of image processing using thresholds often includes a binary map of the inspection points 18 corresponding to the value of one dimensional data, e.g., each pixel represents intensity of a particular optical signal above or below a given threshold. This procedure often corresponds to common sense visual observations about the material being inspected. An example would be searching for undesirable dark spots in a cloth fiber.

Unfortunately, when applied to lumber defect inspection, the relative brightness of a given inspection point may have no meaning without consideration of a substantial number of neighboring points for their individual brightness or for the shape or size of a group of these points that may constitute a particular defect. This makes image processing procedures as applied to lumber defect scanning time consuming, complex, and susceptible to error.

The present invention, however, classifies individual inspection points 18, on the basis of the data from that point only or from average values of the data from nearby neighbors according to a branch of pattern recognition called multivariate analysis. Such classifications are successful, even when the relationships or correlations among the data are so complex and multi-dimensional to make impossible visualization by a human being. In other words, interrelationships among the data may be impossible to visualize, understand, or explain, but the process of multivariate pattern recognition correlates scan vector data and training set data to establish characterization of an inspection point 18.

Multivariate analysis of the optical data proceeds as described above by "training" the analysis procedure on a sample of each of the lumber defects of interest. This training procedure, also known as supervised classification, requires a human operator to identify a particular region of interest, i.e., define a training set vector. The training set vector or vectors correspond to one or more examples of the defect to be classified. The training set vector is selected, for example, by moving joystick 80c to locate a cursor on computer display terminal 80b displaying one of the optical data sets as a gray scale image.

A statistical procedure is then used to find a combination of the multidimensional data that optimally describes the data vectors within the training set. A number of statistical procedures are available for this step, for example K Nearest Neighbor (KNN) or Soft Independent Modeling by Class Analogy (SIMCA). Selection of an appropriate procedure for a given classification problem like lumber defect inspection involves minimizing the error in classification by choosing the data dimensions (measured variables) that provide the most information, and by selecting a classification that is best suited for these data.

Classification then proceeds by applying a similar analysis to each of the inspection points, i.e., each scan vector (a test set), also selected by an operator or by considering all of the scan vectors taken from an article 12. The result of this analysis is a measure of distance (in n-dimensional space) of the scan vector data points (test set points) from the training set vector for each of the defects. This resulting "distance" (or inversely, similarity) can be used to classify areas on surface 16 as being one of the known defects of interest or clear wood (which can also be identified via a training set vector). A statistical probability for this classification can also be derived.

Pattern recognition analysis may be conducted, for example, according to what is referred to as "cluster analysis." Under such cluster analysis, data values in a training set vector define data points in an n-dimensional space. The axes of this n-dimensional space are manipulated, i.e., rotated, until a measure of separation between data points of the training set vector is minimized. A variety of methods may be employed to determine distance between data points in n-dimensional space, e.g., widest separation, average separation, or sum of separations. Once one or several dimensional axes rotation functions are found to sufficiently minimize the distance between data points for a given training set vector, these functions are associated with that training set vector for use against data values held in a scan vector. To apply data values of a scan vector to an axes rotation function associated with a given training set vector, the same dimension axes rotated by the function associated with the training set vector are selected for rotation relative to the scan vector data values. If rotation of the scan vector axes of rotation results in sufficiently minimal clustering of the data points thereof, then the scan vector is considered to be similar to the training set vector. The extent of similarity between a given training set vector and a given scan vector may be expressed as a probability based on the difference in clustering provided by a given axes rotation function against the training set vector data values versus the scan vector data values. In other words, distance is considered the inverse of similarity.

Image processing techniques can then be applied, if necessary, to assist in classification of these defect areas by their shape and size. Note that these techniques are more likely to be correct if other classification means have already been used to identify a region or interest.

It can be appreciated that multivariate signal processing techniques can take substantial processing time if not applied in an optimal way. Preprocessing of the data can reduce this processing time and decrease the classification error. For example, identifying knots using grain defect scanning techniques and applying multivariate analysis or other classification techniques like image processing to a limited set of defects (not including knots) for the remaining surface of the board under inspection improves accuracy and processing time.

It will be appreciated that the present invention is not restricted to the particular embodiment that has been described and illustrated, and that variations may be made therein without departing from the scope of the invention as found in the appended claims and equivalents thereof. For example, U.S. Pat. No. 5,252,836 shows a more practical form of reflective grain defect scanning provided by a flying-spot laser scanner. It will be understood, therefore, that additional detectors shown herein, e.g., providing outputs H, T, C1, C2, and C3, may be incorporated into a flying-spot laser scanner in the manner in which detectors 22 and 24 are shown in U.S. Pat. No. 5,252,836 in the form of a flying-spot laser scanner.

What is claimed is:

1. A method for identifying a defect relative to a given wood article, said method comprising the steps:

collecting a first set of sensor data values taken from sensors directed toward a portion of a sample wood article surface, said portion of said sample wood article surface corresponding to a known defect, said set of sensor data values including a first specular reflection value and a first diffuse reflection value each representing wood grain structure at said portion of said wood article;

selecting at least one mathematic function applied to said set of sensor data values and providing a given distance therebetween;

collecting a second set of sensor data values taken from sensors directed toward a portion of said given wood article, said second set of sensor data values corresponding to said first set of sensor data values and including a second specular reflection value and a second diffuse reflection value;

applying said mathematic function to said second set of sensor data values; and if said at least one mathematic function indicates distance between said second set of sensor data values at or below said given distance then identifying said portion of said given wood article as corresponding to said known defect.

2. A method according to claim 1 wherein said first set of sensor data values include a calculated ratio of said first specular reflection value and said first diffuse reflection value and said second set of sensor data values include a calculated ratio of said second specular reflection value and said second diffuse reflection value.

3. A method according to claim 2 wherein said first set of sensor data values include a first measure of height and said second set of sensor data values include a second measure of height.

4. A method according to claim 3 wherein said first set of sensor data values include a first measure of tracheid effect and said second set of specular data values include a second measure of tracheid effect.

5. A method according to claim 1 wherein said method comprises selecting said mathematic function according to multivariate pattern recognition analysis.

6. A method according to claim 4 wherein said first sensor data values include first image value and said second set of sensor data values includes a second image value.

7. A method according to claim 6 wherein said first and second image values correspond to light intensity in a given color band.

8. A method for detecting presence of at least one of a set of wood cell structure conditions at a wood article surface, said method comprising the steps:

executing a training session wherein for each member of said set of wood cell structure conditions at least one training vector is defined, each training vector including a designation of the associated wood cell structure condition and a set of training vector sensor data values taken from sensors directed toward an example of the associated wood structure condition, said training vector sensor data values including a first specular reflection value and a first diffuse reflection value each representing wood cell structure at said example of the associated wood structure condition;

executing a scanning procedure against inspection points of said given wood article wherein a scan vector is collected for each inspection point, each scan vector including location data indicating a physical location for the associated inspection point and including a set of scan vector sensor data values taken from sensors directed toward the associated inspection point and corresponding to said training vector sensor data values and including a second specular reflection value and a second diffuse reflection value;

matching by pattern recognition analysis each scan vector with each training vector; and detecting presence of a given wood structure condition at a given location when a training set vector corresponding to said given wood structure condition matches under said pattern recognition analysis a scan vector for said given location.

9. A method according to claim 8 wherein each training vector includes a calculated ratio of said first specular reflection value and said first diffuse reflection value and each scan vector includes a calculated ratio of said second specular reflection value and said second diffuse reflection value.

10. A method according to claim 9 wherein each training vector includes a first measure of height and each scan vector includes a second measure of height.

11. A method according to claim 10 wherein each training vector includes a first measure of tracheid effect and each scan vector includes a second measure of tracheid effect.

12. A method according to claim 11 wherein each training vector includes a first image value and each scan vector includes a second image value.

13. A method according to claim 12 wherein said first and second image values represent a magnitude of light intensity in a first color band.

14. A method according to claim 13 wherein said first and second image values represent a magnitude of light intensity in a second color band.

15. A method according to claim 8 wherein said pattern recognition is by multivariate pattern recognition.

16. A method of identifying the condition of inspection of inspection points of a wood article surface, the method comprising the steps:

scanning a plurality of inspection points of said wood article surface, said scanning step collecting for each inspection point both reflective grain defect data and tracheid effect data;

identifying a first class of surface conditions by reference to said grain defect scanning data; and identifying a second class of surface conditions by reference to said tracheid effect data while excluding from consideration said first class of surface conditions said first class of surface conditions being more reliably detected relative to said second class of surface condition.

17. A method according to claim 16 wherein said first class of surface conditions corresponds to knot defects.

18. A method according to claim 16 wherein said second class of surface conditions to broad-area defects.

19. A method according to claim 18 wherein said broad area defects includes at least one of wane, wood decay, stains, and compression wood.

* * * * *

UNITED STATES PATENT AND TRADEMARK OFFICE
CERTIFICATE OF CORRECTION

PATENT NO. : 5,703,960
DATED      : December 30, 1997
INVENTOR(S) : Soest

It is certified that error appears in the above-identified patent and that said Letters Patent is hereby corrected as shown below:

```
Col. 16, line 26, delete "of inspection".

Col. 16, line 45, after "conditions" insert
   --corresponds--.
```

Signed and Sealed this

Tenth Day of March, 1998

Attest:

Attesting Officer

BRUCE LEHMAN

Commissioner of Patents and Trademarks